United States Patent

Ito et al.

[11] Patent Number: 5,814,327
[45] Date of Patent: Sep. 29, 1998

[54] SHEETS FOR ANIMALS, SHEET, BAGS, DAILY GOODS, INK AND PACKAGING MATERIALS

[75] Inventors: Hiroshi Ito, Tokyo; Kaoru Shinpo, Saitama; Yasuharu Kiritani, Tokyo, all of Japan

[73] Assignee: Daiki Co., Ltd., Japan

[21] Appl. No.: 714,842

[22] Filed: Sep. 17, 1996

Related U.S. Application Data

[62] Division of Ser. No. 608,283, Feb. 28, 1996, Pat. No. 5,595,794, which is a continuation of Ser. No. 271,124, Jul. 6, 1994, abandoned, which is a continuation of Ser. No. 752,466, Aug. 23, 1991, abandoned.

[30] Foreign Application Priority Data

| Dec. 25, 1989 | [JP] | Japan | 1-335965 |
| Jan. 25, 1990 | [JP] | Japan | 2-15592 |
| Apr. 24, 1990 | [JP] | Japan | 2-108190 |
| May 7, 1990 | [JP] | Japan | 2-117113 |
| Jun. 11, 1990 | [JP] | Japan | 2-152367 |
| Jul. 25, 1990 | [JP] | Japan | 2-197061 |
| Aug. 31, 1990 | [JP] | Japan | 2-231888 |

[51] Int. Cl.$^6$ ............ A01K 29/00; A01K 25/34
[52] U.S. Cl. .......... 424/414; 119/165; 119/171; 119/172; 424/411
[58] Field of Search .................. 424/766, 411, 424/414; 119/165, 171, 172

[56] References Cited

U.S. PATENT DOCUMENTS

| 4,622,920 | 11/1986 | Goss | 119/1 |
| 5,143,023 | 9/1992 | Kuhns | 119/173 |
| 5,146,877 | 9/1992 | Jaffee et al. | 119/172 |
| 5,267,532 | 12/1993 | Franklin et al. | 119/173 |
| 5,371,054 | 12/1994 | Plufa et al. | 119/173 |
| 5,685,259 | 11/1997 | Santioemmo et al. | 119/172 |

*Primary Examiner*—Robert H. Harrison
*Attorney, Agent, or Firm*—Bierman, Muserlian and Lucas

[57] ABSTRACT

Since the present invention is composed of required component capable of changing in color with which a daily product and so on are impregnated, painted or printed, such daily product is convenient in daily life by indicating a contact between the required component and urine and so on.

1 Claim, 6 Drawing Sheets

SHEETS FOR ANIMALS, SHEET, BAGS, DAILY GOODS, INK AND PACKAGING MATERIALS

PRIOR APPLICATIONS

This application is a division of U.S. patent application Ser. No. 608,283 filed Feb. 28, 1996, now U.S. Pat. No. 5,595,794 which is a continuation of U.S. patent application Ser. No. 271,124 filed Jul. 6, 1994 which is a continuation of U.S. patent application Ser. No. 752,466 filed Aug. 23, 1991, both now abandoned.

SPECIFICATION

1. Title of the Invention

Sheets for animals, sheet, bags, daily goods, ink and packaging materials

2. Field of the Invention

The present invention relates to sheets for animals such as pet animals, sheet and bags for impregnating tissue with nail polish remover, sterilizer, perfume and the like, sand for pet animals or humans, daily goods such as toilet sheet covers and toilet papers, and packaging materials for fruits, chemicals, cement and the like as well as ink therefor.

BACKGROUND OF THE INVENTION

Conventional sheets for animals such as pet animals consist of mesh sheets and the like.

However such conventional sheets have a problem in that the components of urine and so on excreted from the animals can not be detected qualitatively or quantitatively and the condition of the animals can not be detected.

An object of the present invention is to provide sheets for the animals which can detect the components of the excretions excreted from the animals in order to detect the condition of the animals. Conventional nail polish remover is liquid type materials filled in a bottle, from which the content remover fluid is taken to impregnate the tissue for use.

The tissues are also used to wipe or clean dirty parts after excretion.

However the liquid type nail polish removers mentioned above are not convenient for carrying since they are provided as bottles and most of the tissue have no sterilizing effect.

It is an object of the present invention to provide a sheet and bag material suitable for carrying, which can be painted with the nail polish removers, sterilizer, perfume and the like.

Some of conventional diapers or bed sheets used for animals and humans are in forms of mesh-like sheets.

However such conventional diapers or bed sheets also have a problem in that the excretion of the animal can not be detected and the components of the urine and so on can not be detected qualitatively or quantitatively and thus the condition of the animal can not be detected.

It is another object of the present invention to provide daily goods capable of detecting the conditions and so on of the animals or humans by detecting the moisture for the purpose of conducting appropriate treatment.

Conventional packaging materials for fruits, chemicals and cement and the like consist of paper and so on, which is formed into a bag and so on.

However such conventional materials have a problem in that they can not detect the moisture of them.

It is another object of the present invention to provide a packaging material capable of detecting the moisture.

DISCLOSURE OF THE INVENTION

Thus the present invention provides sheets for animals comprising a first sheet having fluid-permeability and a second sheet having no fluid-permeability between which a third sheet consisting of one or more layers is provided wherein one or more of the first, second and third sheets are impregnated, painted or printed with required component.

According to the present invention, urinary PH, protein, glucose and blood are detected qualitatively or quantitatively upon contact between the excreta from animals and so on and the required component of the sheet, and sterilizer, perfume and deodorant effects are optionally be provided.

A sheet or bag of the present invention have a capsule into which a liquid or powder form of the required component is filled and which is broken by external force to disperse the required component. Thus the present invention can conveniently be carried and a certain amount of the required component in the liquid or powder form can be applied to or impregnate the papers such as tissues only by breaking the corresponding caps.

A daily product of the present invention consists of material impregnated, painted or printed with required ink capable of changing in color depending on moisture.

Therefore the daily product changes the material in color upon contact between the moisture of excreta and so on from the animal and so on and the required ink present in the product, whereby detecting urinary PH, protein, glucose and blood qualitatively or quantitatively, indicating the condition of the animal or human and being helpful to conduct various treatments appropriately.

Also by using the required ink, printing on the daily consumable goods can be made at a low cost, so the daily goods provides reasonable prices for quantitative or qualitative detection of protein, glucose and blood on a routine life.

In some of the examples of water-soluble sheets, a low cost advertisement by patterns or letters which were printed with the required ink is made.

A packaging material according to the present invention consists of a material on which the required component capable of developing color by moisture is impregnated, painted, or printed.

Therefore the packaging material of the present invention can indicate the presence of the moisture impregnating the material, which provides a useful information for the various treatments.

Accordingly, the packaging material indicates an exact point when or where goods got wet during the shipping, telling who is responsible.

When the goods is not water-resistant, the wet becomes distinct, so the goods can be treated.

By printing the address where the goods is received, the bags and so on are not necessary to be prepared at the address, whereby reducing the stock.

PREFERABLE EMBODIMENTS OF THE PRESENT INVENTION

The Present Invention is further described based on the examples with referring to the appended figures.

Figure 1:
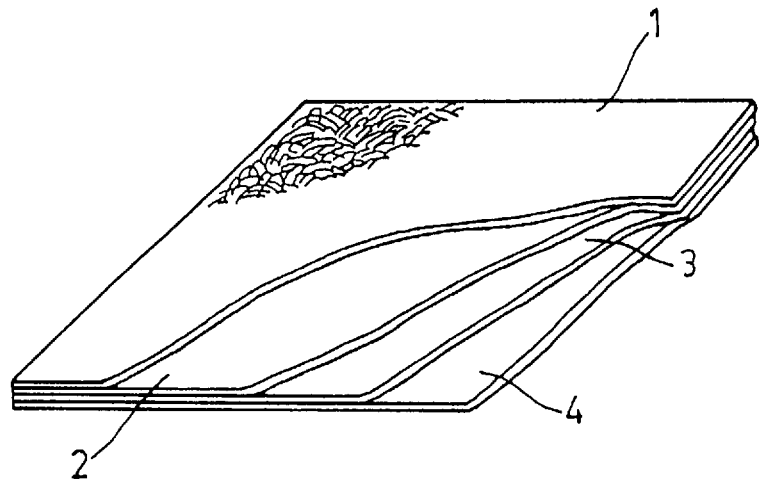
FIG. 1 is a perspective view of sheets for animals of the present invention including a partial sectional view.

FIG. 1 is a perspective view of an embodiment of the present invention including a partial sectional view.

The sheets for animals of this embodiment consists of the first sheet which has permeability of the excreta, for example, urine of the animals and is a polymer-containing sheet 1 made from rayon and the like, the second sheet which is a synthetic resin film 4 having no fluid permeability, and the third sheet which is sandwiched between the first sheet, namely polymer-containing sheet 1 and the second sheet, namely synthetic resin film 4 and which consists of one or more layers comprising paper 2 and polymer-containing sheets 3.

Furthermore at least one of the first sheet, namely polymer-containing sheet 1, the second sheet, namely synthetic resin film 4 and the third sheet comprising the paper 2 and polymer containing sheet 3 is impregnated, painted or printed with the required component.

The third sheet may consist of one or more layers of paper or non-woven fabric, and thus the number of layers is not particularly specified.

The first to third sheets are not limited to the paper, polymer-containing sheet and film mentioned above.

The required component should be any reagent which can be used to detect qualitatively or quantitatively urinary PH, protein, glucose and blood as well as other reagents such sterilizer, perfume, deodorant agents and the like. However the required component is not limited to the above.

The reagents for urine tests include for example methy-1red and bromothymol blue for detecting urinary PH, tetrabromophenol blue for detecting urinary protein, glucose oxidase, peroxidase and potassium iodide for detecting glucose, and 3,3', 5,5'-tetramethylbenzene for detecting urinary blood.

Furthermore in detail, the ink is used for the detecting layer and the ink consists of bromothymol blue and cellulose or derivatives of the cellulose which are dispersed or dissolved in organic solvent and change the color of the detecting layer.

Figure 2A:
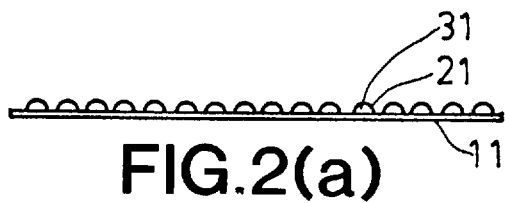
FIG. 2(a) is a sectional view by line A—A of a plan view shown in FIG. 2(b) of another embodiment of the present invention.
Figure 2B:
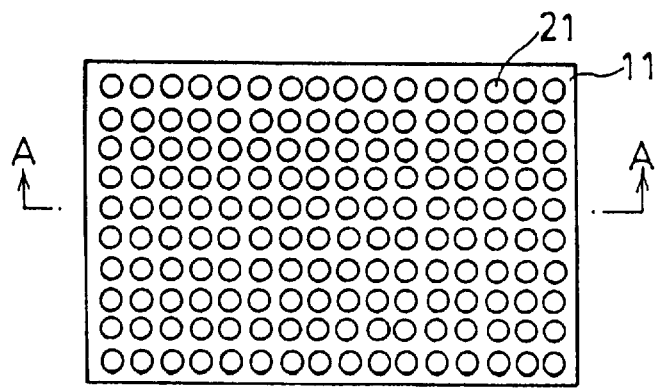

FIG. 2(a) is a sectional view by line A—A of FIG. 2(b) showing another embodiment of the present invention.

The required component 31 in a liquid or powder form is filled in a sheet 11 and a capsule 21 is placed on the sheet 11 and the capsule 21 is broken by external force to sprinkle the component.

The materials for the sheet 11 may be, for example, paper, non-woven fabric, cloth, synthetic resin such as vinyl resin, aluminium foil and the like.

The capsule 21 may be made from synthetic resin such as vinyl resin, aluminium foil and the like.

The required component 31 may be sprinkled, painted or impregnated to the tissue paper, toilet paper and the like.

Two or more of the sheet 11 as shown in FIG. 1(a) may be overlaid and used as a set. In such case, different required component may be used in the each different sheets 11.

The required component 31 consists of, for example, nail polish remover, sterilizer, deodorant, perfume, soap, antimis agent for glasses, oil film remover, shoe polisher, and fire distinguishing agent.

The nail polish remover consists of moisturizing agents such as liquid lanoline, polyethylene glycol, collagen and so on.

The sanitary agent is impregnated and painted with the toilet paper. The toilet paper is used when human excretes.

The sanitary agent consists of water, deodorant, sterilizer, oil and so on. The sterilizing agent which is impregnated and painted with the toilet paper for cleaning the toilet pot consists of ethanol, water, isopropyl alcohol, DL-pyrrolidone carboxylate and the like.

The perfume for sterilizing the toilet consists of aroma components, water, alcohols and so on. The antimist agent for glasses consists of fluorine based surfactant, water and ethanol.

The oil film remover consists of surfactant, inorganic builder, preservative, abrasives such as silicon dioxide and so on, chelating agent and silicate.

The cosmetic liquid consists of paraben, polyethylene glycol, aromatics and so on.

The stain remover consists of chlorine-based or oxygen-based remover, alcohols, water and so on.

The shoe polisher consists of wax, fat, organic solvents and so on.

The fire distinguishing agent consists of ammonium phosphate and potassium carbonate, and may be in the from of powder or liquid.

When the sheet 11 having the capsules 21 filled with fire extinguishing agent is used to wrap a flammable product, the sheet 11 has the firefighting effect.

These required components are not limited to the above.

Figure 3A:
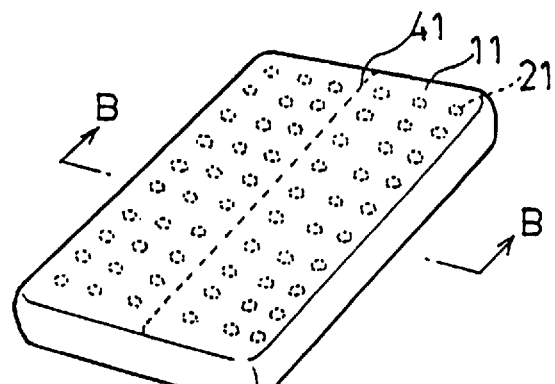
FIG. 3(a) is a perspective view of still another embodiment of the present invention.
Figure 3B:
FIG. 3(b) is a sectional view by line B—B of FIG. 3(a).

FIG. 3(a) is a sectional view by line B—B of FIG. 3(b) showing another embodiment of the present invention.

A sheet 11 is formed into a bag, in which tissue papers 51 are packed. When a cutting line 41 is broken, the required tissue papers 51 are taken from the bag.

Figure 4:
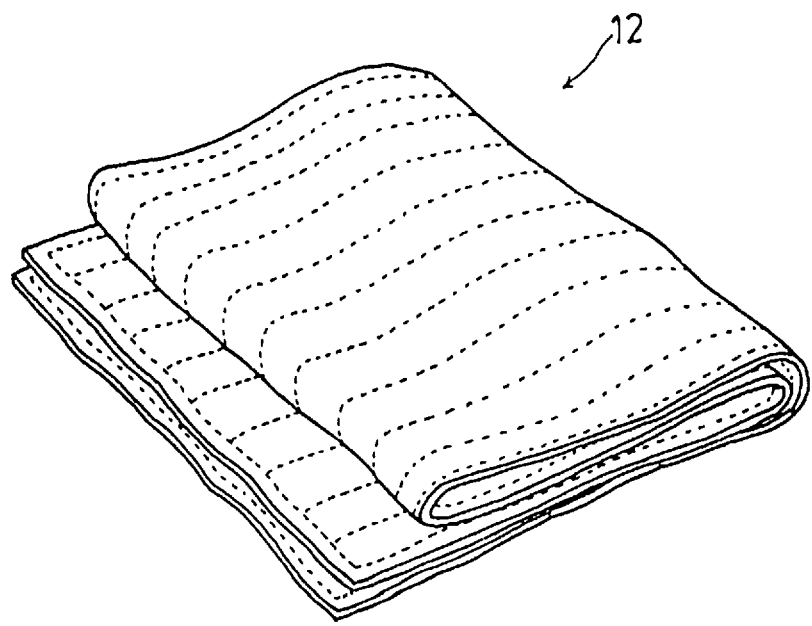
FIG. 4 is a perspective view of an embodiment of a towel of the present invention.
Figure 5:
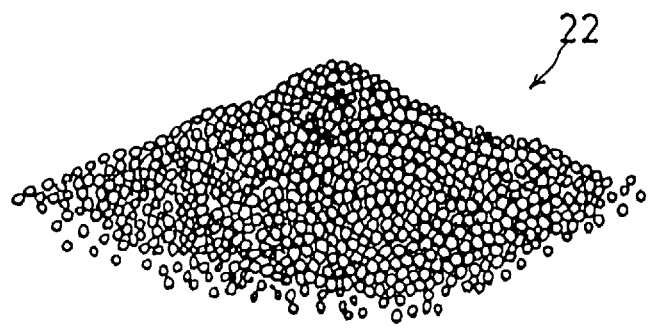
FIG. 5 is a perspective view of an embodiment of the sands for a pet toilet of the present invention.
Figure 6:
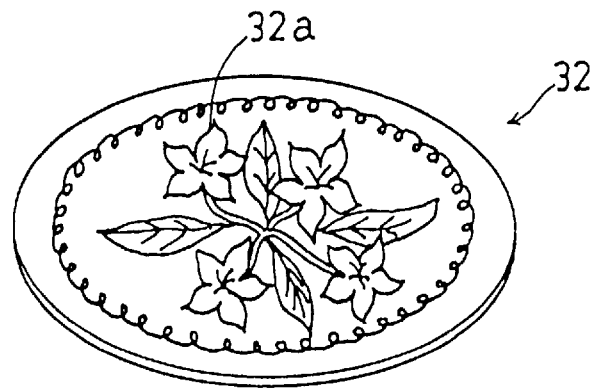
FIG. 6 is a perspective view of an embodiment of a coaster or water-soluble sheet of the present invention.
Figure 7:
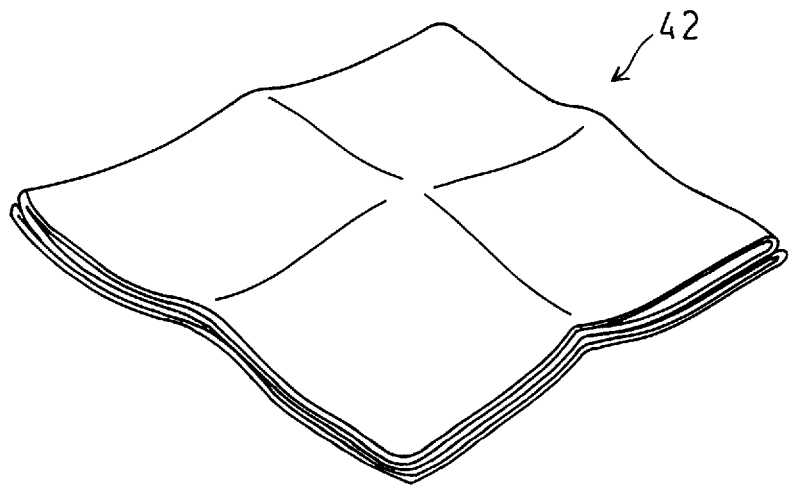
FIG. 7 is a perspective view of an embodiment of a napkin of the present invention.

The construction of the bag is not limited to the above. FIG. 4 is a perspective view of an embodiment of a towel 12 of the present invention, FIG. 5 is a perspective view of an embodiment of sands 22 for a pet toilet of the present invention, FIG. 6 is a perspective view of a coaster 32 of the present invention, and FIG. 7 is a perspective view of an embodiment of a napkin 42 of the present invention.

These embodiments consist of the materials which are impregnated, painted or printed with the required component capable of changing color of the materials by the required water. Such materials consists of, for example, paper, non-woven fabric and the like.

The required component may be any reagent which can be used to detect qualitatively or quantitatively urinary PH, protein, glucose, blood and so on as well as other agents such as sterilizer, perfume, deodorant agents and the like. The required components are not limited to the above.

Furthermore going into detail, the ink is used for the detecting layer, and consists of bromothymol blue, cellulose and derivatives of the cellulose which are dispersed or dissolved in organic solvent and change in color at the detecting layer.

The required components for developing color may be, for example, quinaldine red, stainsall, 3-nitrosalicylaldehyde, ethylred, m-nitrophenol, phenolphthalein, ethylbisacetate, thymolphthalein and the like.

In the embodiment, the toilet sand 22 for animals in FIG. 5 is impregnated with the required color-developing component, which develops the color at only part of the sand 22 to where the urine of the pets touches, and the sand of the part can be discarded.

Also as shown in FIG. 6, only pattern 32a of the coaster 32 impregnated with the required component changes the color and exhibits beauty when the required water touches the pattern 32a.

FIG. 5 is perspective view of an embodiment of the sand 22 for pet toilet of the present invention.

Figure 8:
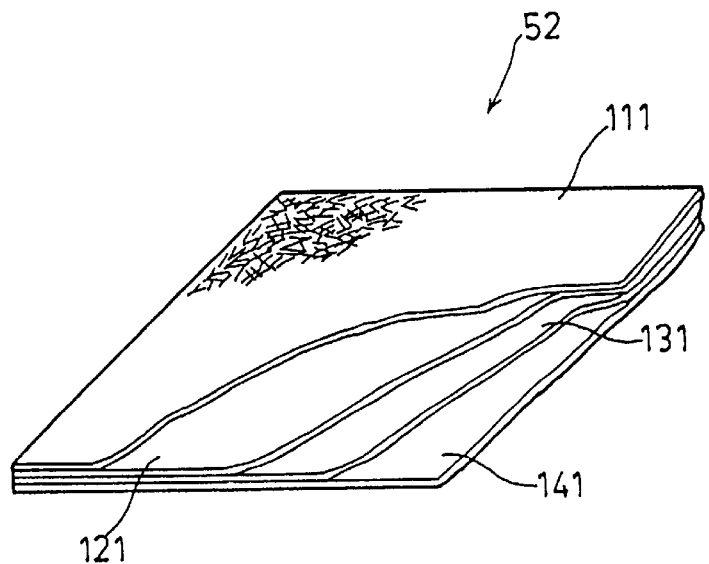
FIG. 8 is a perspective view of an embodiment of a diaper of the present invention including a partial sectional view.

FIG. 8 is a perspective view of an embodiment of the diaper 52 of the present invention including a partial sectional view.

This embodiment consists of a first sheet, i.e. polymer-containing sheet 111 made from rayon and the like which have fluid-permeability and through which the excretes of the animals, for example, urine and so on pass, a second sheet, i.e. synthetic resin film 141 having no fluid-permeability, and a third sheet consisting of one or more layers, i.e. a paper 121 and a polymer containing sheet 131, which is provided between the first sheet, i.e. the polymer-containing sheet 111 and the second sheets, i.e. the synthetic resin film 141.

Furthermore one or more of the first, second and third sheet, namely, the polymer-containing sheet 111, the synthetic resin film 141 and the paper 121 and the polymer-containing sheet 131 may be impregnated, painted or printed with the required ink.

The number of layers of the third sheet may not be specified as long as the third sheet consists of one or more layers of the paper and the polymer-containing sheet.

The materials of the first to third sheets are not limited to the paper, polymer-containing sheet or film mentioned above.

These embodiments consist of the materials which can be impregnated, painted or printed with the required ink which changes the color by the required water.

The required ink can be composed by dispersing or dissolving indicators for detecting urinary PH, protein, glucose, blood, urobilinogen or ketone body together with cellulose and derivatives thereof in organic solvent.

In the embodiment mentioned above, the indicators for urinary PH may be, for example, phenolphthalein, bromothymol blue, bromocresol purple, tetraiodophenolsulfone phthalein, brilliantyellow, phenol red, cresol red, ethyl orange and the like.

In some conventional indicators, the color may fade within several minutes after the change of the color by detecting the required water. Bromocresol purple as the indicator preventing from fading can be effectively used together with other indicators mentioned above. The time point for judgment of the change of the color is not limited to the time right after the change.

The indicator for detecting urinary protein includes tetrabromophenol blue and so on. The indicator for detecting urinary glucose includes glucose oxidase, peroxidase, 2.7-diaminofluorene dihydrochloride, sodium N-(3-sulfopropyl) -3,3', 5,5'-tetrametheylbenzidine and so on. The indicator for detecting urinary blood includes cumene hydroperoxide, tetramethylbenzen and so on. The indicator for detecting urinary urobilinogen includes methanoic acid, 3,4-methylened ioxybenzene diazonium tetrafluoroborate and so on. The indicator for detecting urinary keton body includes glycine, sodium nitrobromide and so on.

For example, the combination of tetrabromophenol blue and citric acid buffer solution of PH 3 can be used to detect protein by means of protein differentiation.

In the presence of peroxidase in urinary hemoglobin, cumene hydroperoxide is oxidized and indicator 3,3', 5,5'-tetramethylbenzidine changes into oxidized form of 3,3', 5,5'-tetramethylbenzidine, whereby developing blue color.

The glucose is reacted with oxygen in air by catalyst of the glucose oxidase to form hydrogen peroxide, which oxidize chromogen by catalyst of peroxidase, resulting in oxidized iodine complex.

In order to make the indicators into ink, the indicators mentioned above is dispersed or dissolved together with cellulose and derivatives thereof in organic solvent and the mixture forms a detecting layer which changes the color.

The resins useful in the present embodiment include cellulose and derivatives thereof, urethanes and polyamides.

The cellulose, hydroxypropyl cellulose, methylcellulose, ethyl cellulose, hydroxypropylmethyl cellulose and carboxy methyl cellulose in the cellulose and derivatives there of have high ability of sensitivity.

The solvent depends on the method of printing. For example, although aromatic hydrocarbones can not be used in flexography in view of the characteristic of the plate, the solvent should preferably selected because of the solubility of the resin and stability of the solubility and dispersion of the indicator.

Figure 9:
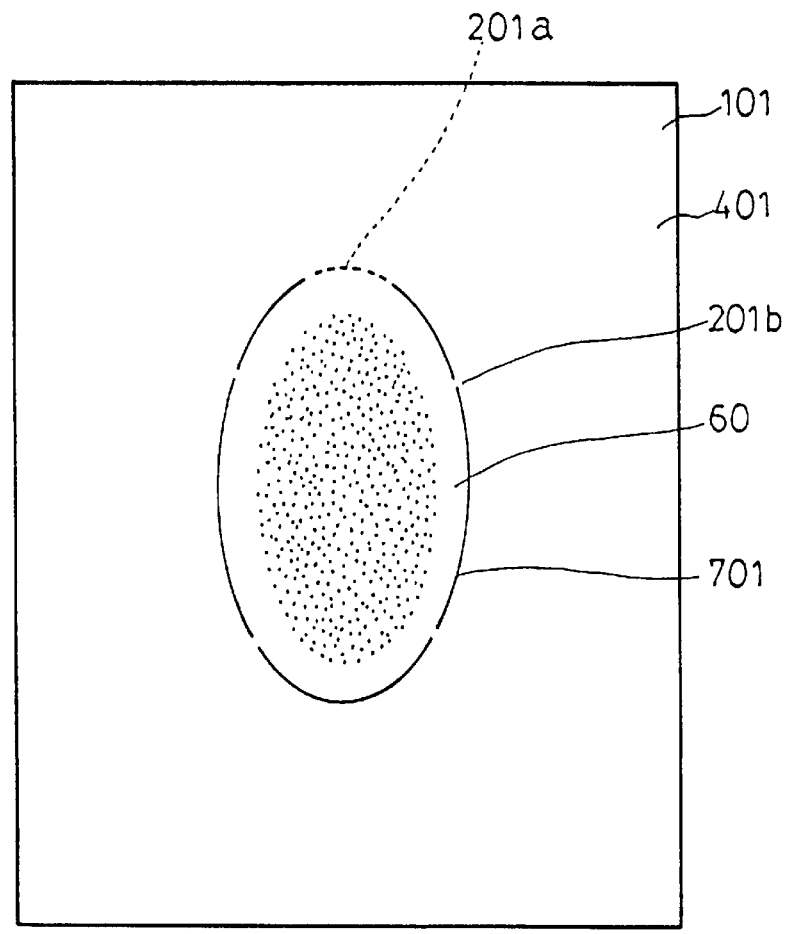
FIG. 9 is a perspective view of an embodiment of a toilet sheet cover of the present invention.

FIG. 9 is a perspective view of an embodiment of the toilet sheet covers of the present invention, and FIG. 6 is a perspective view of a water-soluble sheet 32 of an embodiment of the present invention. Materials of these embodiments are the same as the embodiments mentioned above.

The indicators for urinary PH employed herein, which are difference from those used the embodiments mentioned above, include bromothymol blue, methacresol purple, brilliant yellow, phenol red, tetraiodophenolsulfone phthalein, methylred and ethyl orange and the like.

These indicators are used, when the judgement is done immediately after the change in color.

A toilet sheet covers, as shown in FIG. 9, has a required shaped cutting line 701, along which the sheet 101 is broken to remove a cut-out part 601 to form a opening approximately in the middle of the sheet 101.

The cutting line 701 consists of a dotted line part 201b and a connecting part 201a, whose structures are not particularly limited.

The toilet sheet cover shown in FIG. 9 is mounted on a western style toilet, and the cut-out part 601 is torn off to form an opening, through which the excreta are discharged. At least the cut-out part 601 is impregnated with the required ink.

A circumferential part 401 around the cut-out part 601 may also be impregnated with the required ink.

A water-soluble sheet 32 as shown in FIG. 6 consists of a paper capable of being dissolved rapidly in water, on which patterns or letters 32a are printed with the required ink, which may changes in color when the urine contacts the required ink, whereby we can know the health condition. The sheet 32 can be thrown away into the toilet after that.

The daily goods ate not limited to those mentioned above and, include toilet paper and an umbrella.

The required color-developing components may be, for example, quinaldine red, stainsall, 3-nitrosalicylaldehyde, ethyl red, m-nitrophenol, phenolphthalein, ethylbisacetate, thymolphthalein and the like.

Figure 10A:
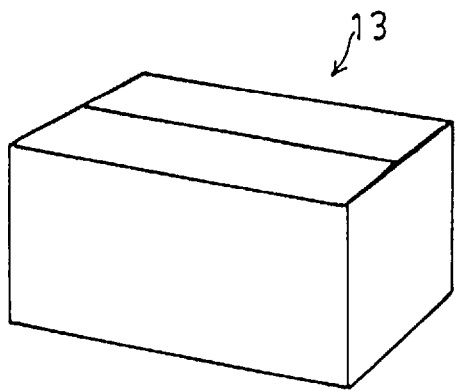
FIGS. 10(a) and (b) are perspective views of an embodiment of a cardboard box of the present invention.

FIGS. 10(a) and (b) are perspective views of the cardboard box of an embodiment of the present invention.

A side surface 13a of the cardboard box 13 consists of an material which is impregnated, painted or printed with the required component capable of developing a color by the water.

The color-developing components, such as quinaldine red, stainsall, 3-nitrosalicylaldehyde, ethyl red, m-nitrophenol, phenolphthalein, ethylbisacetate, thymolphthalein and the like are dispersed or dissolved together with cellulose and derivatives thereof in organic solvent to form the required ink providing a detecting layer which changes in color.

The material consists of, for example, paper, non-woven fabric, linen, synthetic resin and the like.

Figure 10B:
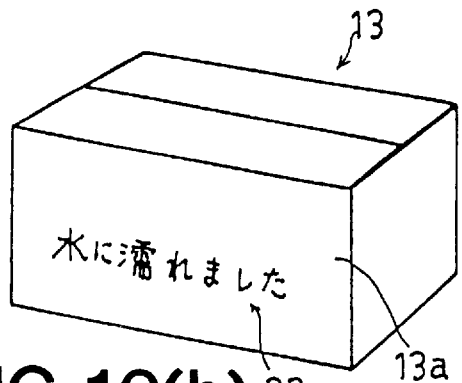

When water contacts with a side surface 1a of a cardboard box 1, indication 23 "The box was wet." appears on the side surface 1a as shown in FIG. 10(b).

Figure 11A:
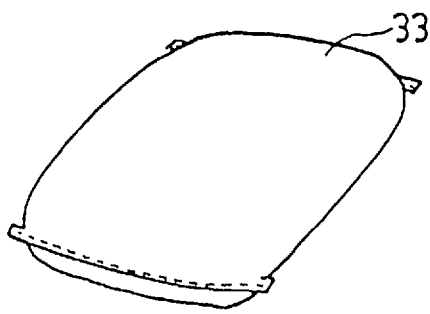
FIGS. 11(a) and (b) and FIGS. 12(a) and (b) are perspective views of an embodiment of a bag of the present invention.
Figure 12A:
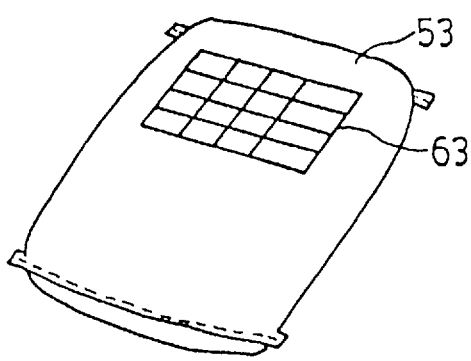

FIGS. 11(a) and (b) and FIGS. 12(a) and (b) are perspective views of an embodiments of bags of the present invention.

Materials and the required components of a bag 33 are the same as those used in the embodiments mentioned above.

Figure 11B:
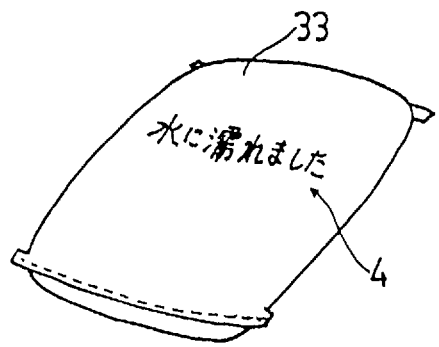

When water contact with a surface 33a of the bag 33, indication 43 "The bag was wet." appears on the surface 33a as shown in FIG. 11(b).

Figure 12B:
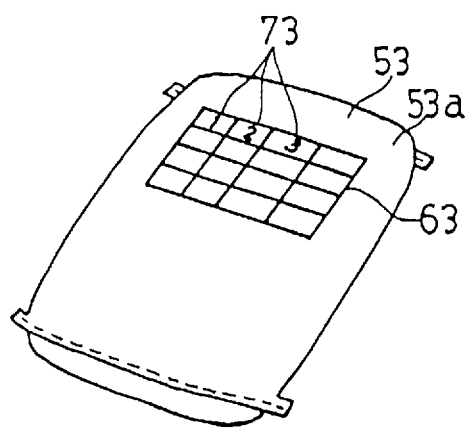

A bag 53 has a surface 53a having informations printed with the required component within a frame 63 previously provided, so informations 73 such as numbers and so on appear when the within of the frame 63 contact with the water as shown in FIG. 12(b).

Figure 13:
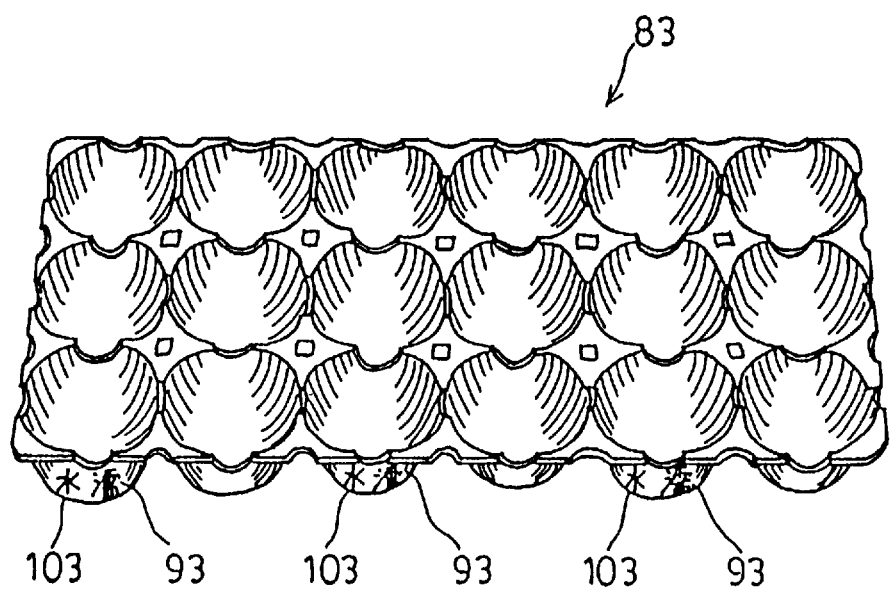
FIGS. 13 is a perspective view of an embodiment of a fruit container of the present invention.

FIG. 13 is a perspective views of an embodiment of the fruit container of the present invention.

An indication 103 representing "wet" appears at a recess 93 of the fruit container 83, when the recess 93 contacts with the water.

The fruit container 83 is formed by molding, although the method of the formation is not limited to the molding.

Alternatively, the bag and so on may initially contain the water with the letters and so on exhibited, which may then disappears when the bag and so on dry.

Materials for the packages are not limited to the one used at the embodiments mentioned above.

Usefulness in Industrial Field

Since the present invention has the required component capable of changing in color with which daily products are impregnated, painted or printed, the present invention provides convenience in daily life by detecting the contact between the required component and the urine and so on when the required component with the urine and so on.

We claim:

1. A toilet sand animals comprising cellulose and cellulose derivatives impregnated with a color-developing component containing bromothymol blue and a sterilizing agent selected from the group consisting of ethanol and DL-pyrrolidone carboxylate, said bromothymol blue and sterilizing agent are dispersed in toluene as organic solvent.

* * * * *